United States Patent
Morrison

(10) Patent No.: US 8,025,683 B2
(45) Date of Patent: Sep. 27, 2011

(54) OPEN AXLE SURGICAL IMPLANT

(75) Inventor: Matthew M Morrison, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 12/768,289

(22) Filed: Apr. 27, 2010

(65) Prior Publication Data

US 2010/0211117 A1    Aug. 19, 2010

Related U.S. Application Data

(62) Division of application No. 11/414,834, filed on Apr. 28, 2006, now Pat. No. 7,731,735.

(51) Int. Cl.
   *A61B 17/70* (2006.01)
(52) U.S. Cl. .................................. 606/278; 606/265
(58) Field of Classification Search .............. 606/104, 606/265, 305
   See application file for complete search history.

(56) References Cited

U.S. PATENT DOCUMENTS

| | | |
|---|---|---|
| 4,050,464 A | 9/1977 | Hall |
| 4,411,259 A | 10/1983 | Drummond |
| 5,020,519 A | 6/1991 | Hayes et al. |
| 5,281,222 A | 1/1994 | Allard et al. |
| 5,380,326 A | 1/1995 | Lin |
| 5,476,462 A | 12/1995 | Allard et al. |
| 5,562,663 A | 10/1996 | Wisnewski et al. |
| 5,616,143 A | 4/1997 | Schlapfer et al. |
| 5,630,817 A | 5/1997 | Rokegem et al. |
| 5,810,878 A | 9/1998 | Burel et al. |
| 5,910,141 A | 6/1999 | Morrison et al. |
| 6,027,533 A | 2/2000 | Olerud |
| 6,036,692 A * | 3/2000 | Burel et al. ............... 606/86 A |
| 6,110,172 A | 8/2000 | Jackson |
| 6,183,472 B1 | 2/2001 | Lutz |
| 6,458,132 B2 | 10/2002 | Choi |
| 6,524,315 B1 | 2/2003 | Selvitelli et al. |
| 6,595,992 B1 | 7/2003 | Wagnet et al. |
| 6,656,179 B1 | 12/2003 | Schaefer et al. |
| 6,755,829 B1 * | 6/2004 | Bono et al. ............... 606/308 |
| 6,783,526 B1 | 8/2004 | Lin et al. |
| 6,790,209 B2 | 9/2004 | Beale et al. |
| 6,958,066 B2 | 10/2005 | Richelsoph et al. |
| 2003/0130659 A1 | 7/2003 | Haider |
| 2003/0199872 A1 | 10/2003 | Markworth et al. |
| 2004/0260285 A1 | 12/2004 | Steib et al. |
| 2005/0149053 A1 | 7/2005 | Varieur et al. |
| 2005/0154389 A1 | 7/2005 | Selover et al. |

FOREIGN PATENT DOCUMENTS

| | | |
|---|---|---|
| EP | 190678 | 3/2002 |
| EP | 1457161 | 9/2004 |
| WO | 2005006948 | 1/2005 |

* cited by examiner

*Primary Examiner* — Eduardo C Robert
*Assistant Examiner* — Elana Fisher

(57) ABSTRACT

A surgical implant engageable by a surgical tool having spaced apart jaws with inward facing tubular protrusions, is provided. The implant includes a body for interfacing with a bone structure. The implant also includes a head connected with the body having spaced apart posts juxtaposed by a stabilization member receiving area. Each post has an outward side face that includes an upper generally vertical surface intersecting with a generally inward directed under surface that in turn intersects with a lower generally vertical surface. The side face has a generally tubular cylindrical indention intersecting the upper vertical surface and the inward directed under surface.

13 Claims, 4 Drawing Sheets

Figure 2A:
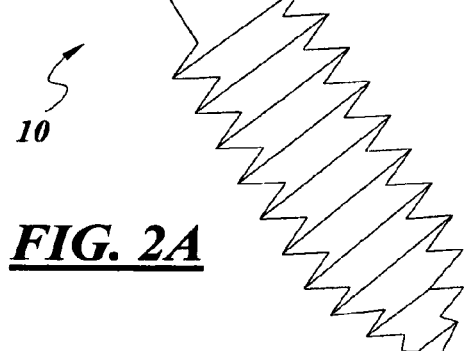
Figure 10:
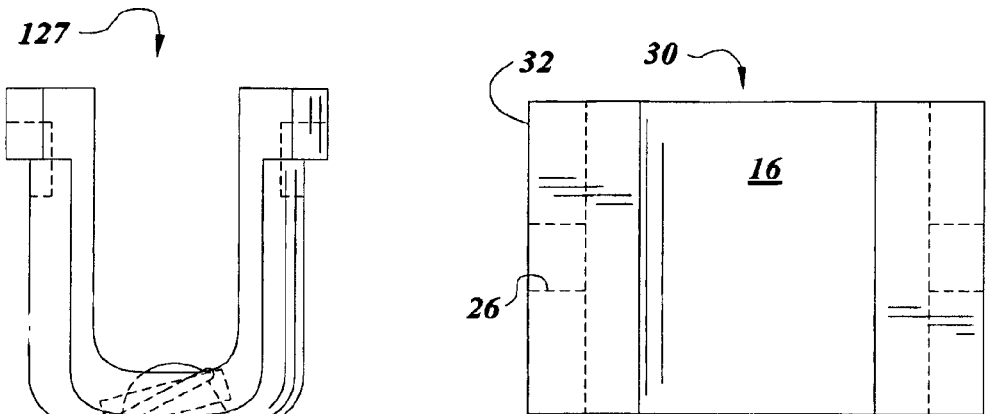

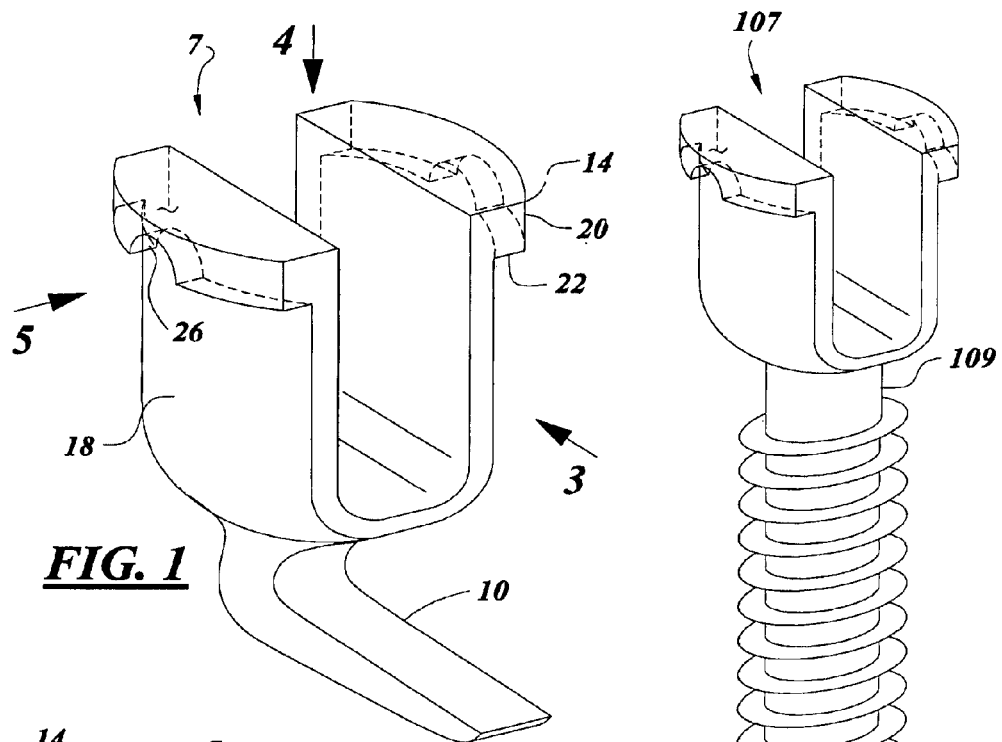
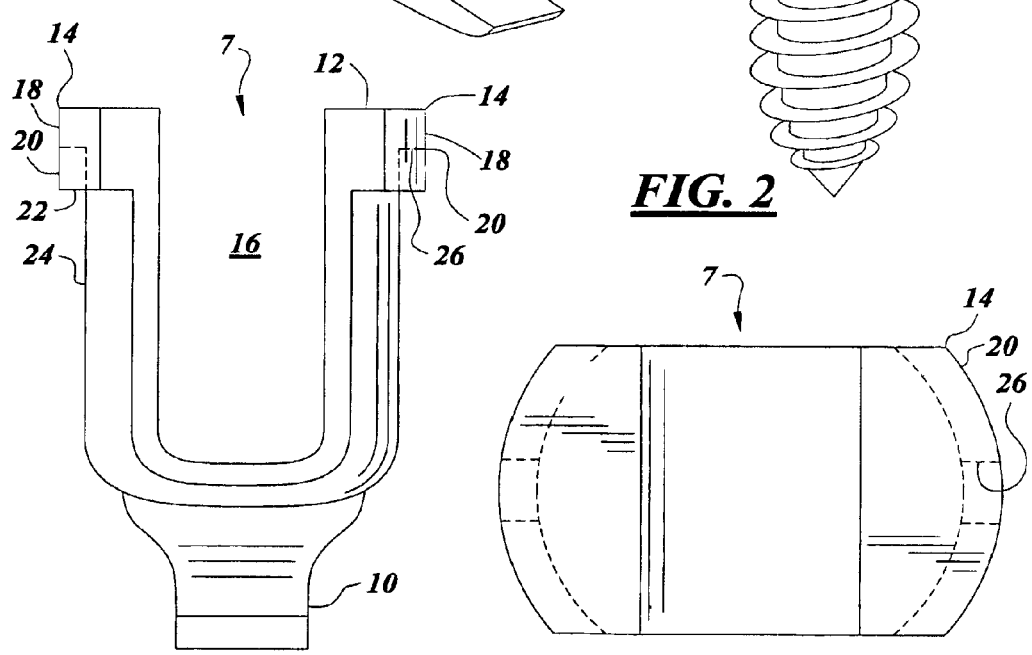
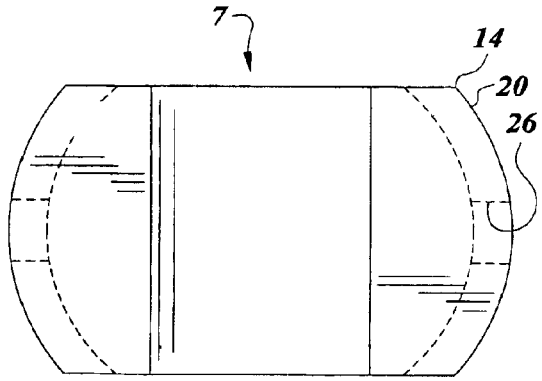
FIG. 1
FIG. 2
FIG. 3
FIG. 4

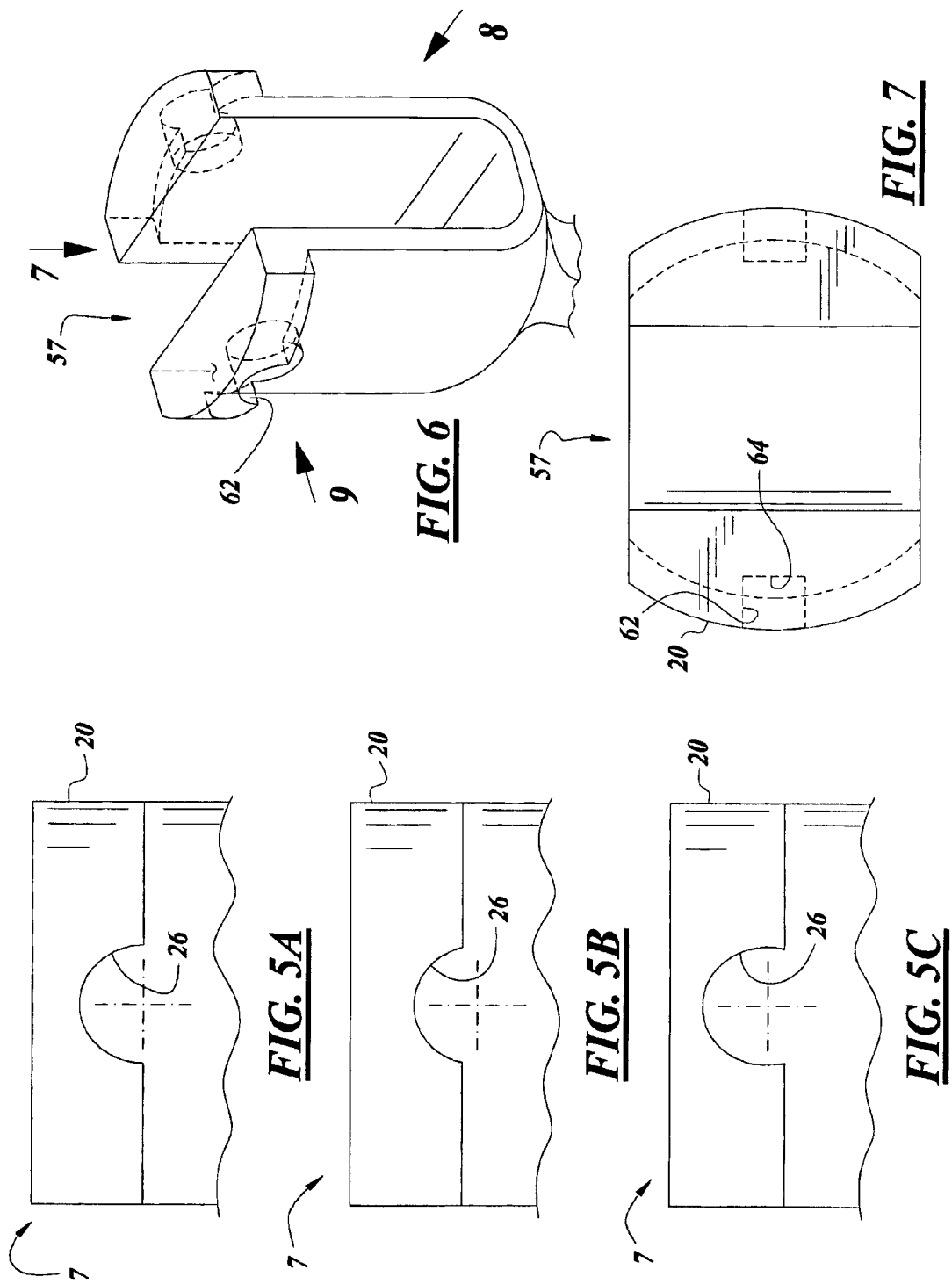

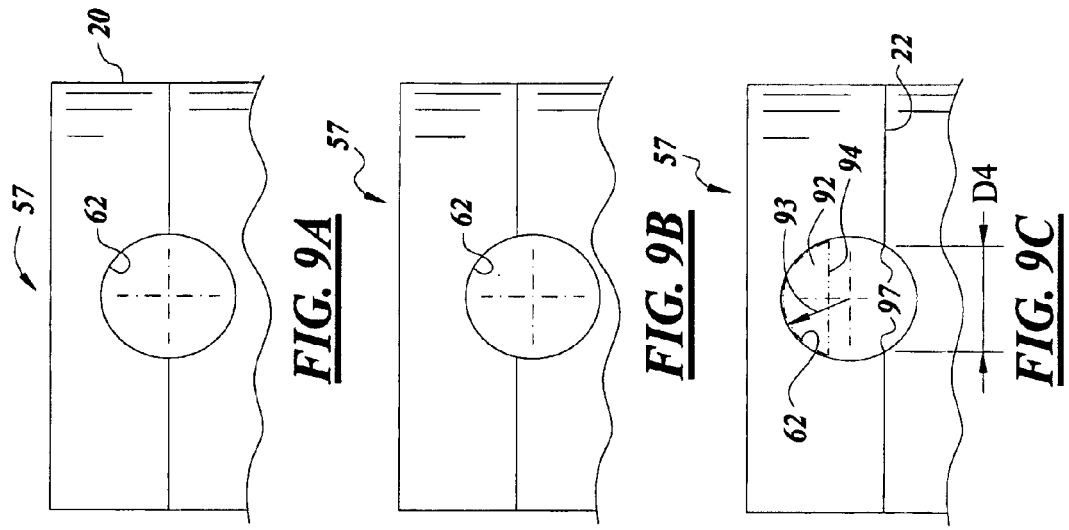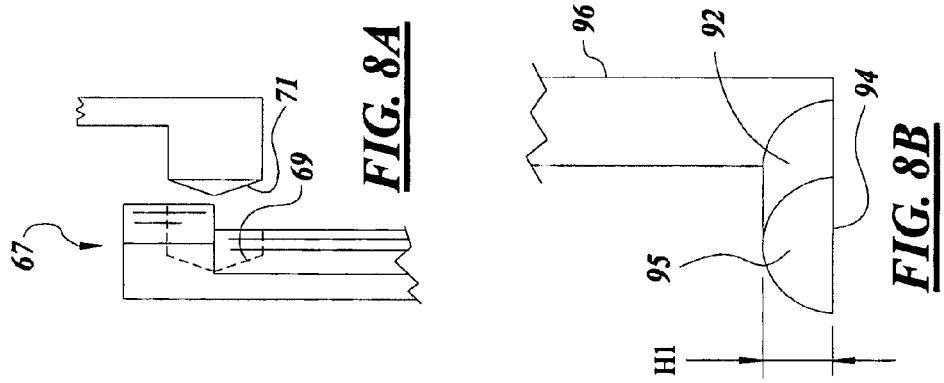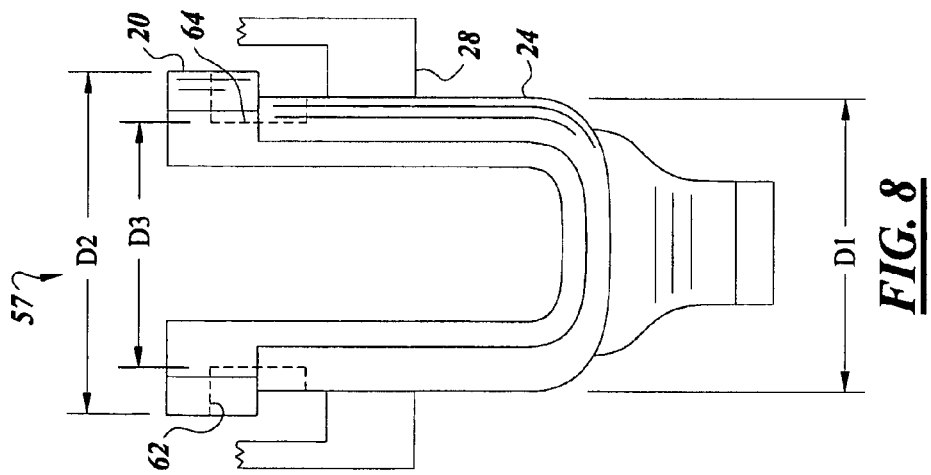

OPEN AXLE SURGICAL IMPLANT

CROSS-REFERENCE TO RELATED APPLICATIONS

This application claims priority to and is a division of U.S. patent application Ser. No. 11/414,834 filed on Apr. 28, 2006, which is hereby incorporated herein by reference in its entirety.

FIELD OF THE INVENTION

The present invention provides a surgical implant that is connectable with a spinal stabilization member such as a cable, rod or plate.

BACKGROUND OF THE INVENTION

Spinal surgeons often treat spinal disorders with spinal fusion augmented with stabilization members such as plates or elongated spinal rods. The stabilization members are connected to the spine with implants such as pedicle screws or lamina hooks. Such "stabilization assemblies" often comprise one or two spinal rods or plates and a plurality of implants engaging the pedicles of their respective vertebral bodies. The implants are provided with U-shaped heads that can be capped to couple the stabilization members to the implants. The heads of the implants are relatively small and are often concealed within the flesh of a patient during a surgical procedure. It is desirable to provide and implant that be torqued or manipulated easily with a surgical tool without making the head of the implant excessively large.

SUMMARY OF THE INVENTION

To make manifest the above noted and other manifold desires, a revelation of the present invention is brought forth. In a preferred embodiment, the present invention provides a surgical implant with an "open axle recess". The implant is engageable by a surgical tool having spaced apart jaws with inward facing tubular protrusions. The implant includes a body for interfacing with a bone structure. The implant also includes a head connected with the body having spaced apart posts juxtaposed by a stabilization member receiving area. Each post has an outward side face that includes an upper generally vertical surface intersecting with a generally inward directed under surface that in turn intersects with a lower generally vertical surface. The side face has a generally cylindrical recess or indention intersecting the upper vertical surface and the inward directed under surface, forming the open axle.

Other features of the invention will become more apparent to those skilled in the art as the invention is further revealed in the accompanying drawings and Detailed Description of the Invention.

BRIEF DESCRIPTION OF THE DRAWINGS

FIG. 1 is a perspective view of a preferred embodiment lamina hook implant of the present invention.

FIG. 2 is a perspective view of a preferred embodiment pedicle screw implant of the present invention.

FIG. 2A is a front elevation view of a preferred embodiment multiple axis pedicle screw implant of the present invention.

FIG. 3 is a front elevation view of the implant shown in FIG. 1.

FIG. 4 is a top plan view of the implant shown in FIG. 1.

FIGS. 5A-5C are partial side elevational views of the implant shown in FIG. 1.

FIG. 6 is a partial perspective view of an alternate preferred embodiment implant of the present invention.

FIG. 7 is a top plan view of the implant shown in FIG. 6.

FIG. 8 is a front elevation view of the implant shown in FIG. 1.

FIG. 8A is a partial front elevation view of another alternate preferred embodiment implant of the present invention.

FIG. 8B is a partial perspective view of a surgical tool and accompanying protrusion which can be used in a particular method of the present invention providing locking between the tool, and implant shown in FIGS. 5C and 9C.

FIGS. 9A-9C are partial side elevational views of the implant shown in FIG. 6.

FIGS. 10 and 11 are views similar to that of FIG. 4 of other alternate preferred embodiment implants of the present invention.

DETAILED DESCRIPTION OF THE INVENTION

Referring to FIGS. 1, 3 and 4, a lamina hook implant 7 of the present invention is provided. The implant 7 has a body 10 for interfacing with a bone structure of a patient. The body 10 is connected with a head 12. The head 12 has spaced apart posts 14. A stabilization member or rod receiving area 16 juxtaposes the posts 14. Each post 14 has an outward side face 18. The outward side face 18 has an upper generally vertical surface 20. The surface 20 intersects a generally inward directed under surface 22. The under surface 22 intersects a lower generally vertical surface 24.

The side face 18 has a generally cylindrical recess or indention 26 penetrating the upper vertical surface 20 and the under surface 22. The indention 26 is torsionally engageable with an inward facing tubular protrusion 28 (FIG. 8) of a surgical tool.

As shown in FIG. 4, the vertical surface 20 has a generally conic curvilinear shape. FIG. 10 is a top view of an alternative embodiment implant 30 having cylindrical indentions 26 wherein the upper generally vertical surface 32 is flat. The body of the implant 30 is substantially identical to the body 10 previously described.

FIG. 5A-5C illustrate three possible partial side views of the implant 7 shown in FIG. 1. In FIG. 5A, the indention 26 projects on the surface 20 180°. In FIGS. 5B and 5C the indention 26 projects on the surface 20 for less than 180° and more than 180° respectively. It is usually preferable that the indention project on the surface 20 between 80° and 240°.

Referring to FIGS. 6, 7, 8, 9A-9C an alternative embodiment implant 57 is provided. The implant 57 is essentially identical to the implant 7 with the exception that the indention 62 of the surface 20 further extends into the lower vertical surface 24 terminating in a blind end 64. FIGS. 9A-9C illustrate the invention 62 projecting onto the surface 20 180°, less than 180°, and more than 180°. It is usually preferable that the indention project on the surface 20 between 80° and 240°.

Referring to FIG. 8, a distance between the two surfaces 24 is D1. The distance between the two surfaces 20 is D2. The distance between the two surfaces 64 is D3. Often during a surgical operation, the implant 57 is concealed within the patient's flesh. A stabilization member such as a cable, plate or an elongated rod extends through the rod receiving area 16. A surgeon uses the stabilization member to aid locating the implant 57. A surgical tool (only partially shown) has the protrusions 28 set at a separation distance closely approximating DI. The surgeon then aligns the protrusions 28 along the lower vertical surface 24. The surgical tool is pulled upward without separating the protrusions 28 a significant distance beyond D1. The protrusions 28 are then pulled up to contact the under surface 24. The protrusions 28 are then turned until they seat into the indentions 62. If the projection of the indention 62 is equal to 180° or less (FIGS. 9A and 9B) the protrusions 28 slides into the indention 62 without requiring an extension of the protrusions outward to a distance D2. After the protrusions 28 are aligned with the indention 62, the protrusions 28 can be moved inward for content with the blind end 64. The inward extension of the protrusions 28 to the blind ends 64 served as a confirming indicator to the surgeon that the protrusions 28 are now ready for torsional engagement with the invention 62. Torsional contact of the protrusions with the indentions occurs from a distance of D2-D3.

In a surgical operation often the rod is very close to the implant 57 and a relatively small force is required to reduce the rod into the rod receiving area 16. In such a case a rod introduction forceps as described in commonly assigned U.S. Pat. No. 6,036,692 Burel et al. (hereinafter referred to as Burel) can be used. In such cases the protrusions of the forceps need only engage with the arcuate portions of the indentions 62 from D1 to D2. In some rod reducing applications, a rod reducing instrument as described in Beale et al. U.S. Pat. No. 6,790,290 (hereinafter referred to as Beale) is more appropriate. The instrument of Beale supplies a large holding force on the implant head. Beale can be modified for its protrusions to initially only engage the indentions in the same area as Burel. Then upon further closure of the arms of Burel's actuator assembly the protrusions will move inwardly to seat in the area of the indentions between D2 and D3.

A further modification can be made to the implant 67 as shown in FIG. 8A so that the indention 62 will have a conic end 69 to mate with a conic end 71 of the protrusion 71 similar to that described in Beale.

FIGS. 5C, 9C and 8B illustrate a further advantage of the present invention. A surgical tool 96 can be provided with protrusions 92 (only one shown) having a radius 93 closely approximating that of the indention 62. The protrusions 92 have a flat 94. The protrusion has a height H1. H1 can be less in length than radius 93. The projection of the indention 62 has a window 97 (the width of the indention 62 at the intersection of the under surface 22 with the upper vertical surface 20) with a width D4. The width of the flat 94 is greater than that of D4. To place the protrusion 92 within the indention the protrusion 92 has a flat contact face 95. The contact face 95 is mated against the surface 24 in a manner similar to that previously described in relation to the protrusion 28. The surgical tool 96 is angled (tilted) to allow the protrusions 92 to enter into the indention windows 97. After the surgical tool 96 is raised back to an upright position the protrusions 92 are essentially locked within the indention 62 since the width of the flat is greater than D4. To remove the tool 96 from the implant 67 the tool 96 is tilted and the protrusions 92 are pushed downward out of the windows 97. The separation distance between the protrusions 92 remain constant. Accordingly, the protrusions 92 can be provided by a connecting rigid non-folding rigid structural member (not shown).

Figure 11:
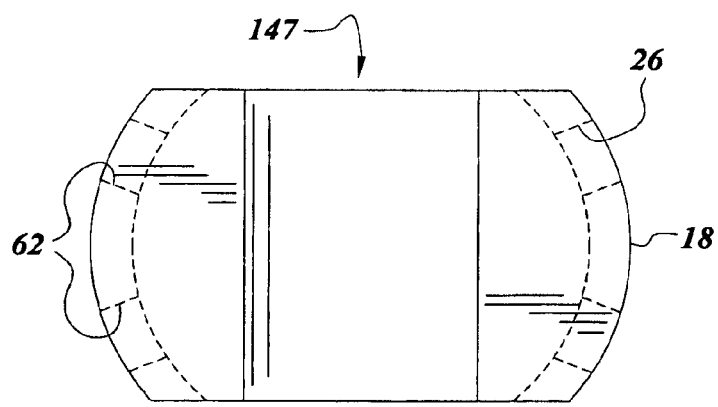

FIG. 2 is pedicle screw 107 embodiment of the present invention having a body 109 for interfacing with a patient's pedicle by threaded insertion. FIG. 2A is multiple axis pedicle screw 127 embodiment of the present invention having a body 129. FIG. 11 illustrates an implant 147 of the present invention having multiple indentions 62 on each side face 18.

While preferred embodiments of the present invention have been disclosed, it is to be understood it has been described by way of example only, and various modifications can be made without departing from the spirit and scope of the invention as it is encompassed in the following claims.

The invention claimed is:

1. A method of engaging a surgical tool having spaced apart jaws with inward facing tubular protrusions with a stabilization member connectable bone interfacing implant, said method comprising:

providing said implant with a body configured for interfacing with a bone structure and a head connected with said body, said head having spaced apart posts juxtaposed by a stabilization member receiving area, each said post having an outward side face, said outward side face having an upper generally vertical surface intersecting with a generally inward directed under surface intersecting with a lower generally vertical surface, said outward side face of each said post having at least one generally cylindrical indention intersecting said upper and lower generally vertical surfaces and said inward directed under surface, each said generally cylindrical indention having a circular profile that penetrates each said upper and lower generally vertical surfaces and terminates in a blind end, said circular profile projecting onto and extending along each said upper and lower generally vertical surfaces, said lower generally vertical surfaces of said posts being spaced apart a distance D1 and said upper generally vertical surfaces being spaced apart a distance D2 greater than said distance D1;

separating said tubular protrusions apart to define a separation distance therebetween closely approximating said distance D1;

positioning said tubular protrusions adjacent said generally lower vertical surfaces defined by said posts of said implant head;

displacing said tubular protrusions in an upward direction along said generally lower vertical surface toward said generally cylindrical indentions while maintaining said separation distance therebetween; and engaging said tubular protrusions at said separation distance with a downwardly facing circular surface defined by said cylindrical indentions.

2. The method as described in claim 1 wherein said blind ends of said generally cylindrical indentions are spaced apart a distance D3 less than said distance D1, and said tubular protrusions are inwardly displaced toward said blind ends thereby providing confirmation of entry of said tubular protrusions into said generally cylindrical indentions by allowing said tubular protrusions to transition to a second separation distance closely approximating said distance D3.

3. The method as described in claim 1 further comprising inwardly displacing said tubular protrusions toward said blind ends and reducing said separation distance to thereby provide confirmation of entry of said tubular protrusions into said generally cylindrical indentions.

4. The method as described in claim 1 wherein said body is a screw.

5. The method as described in claim 1 wherein said circular profile of said generally cylindrical indention projecting onto said upper generally vertical surface extends along an arc of approximately 180°.

6. The method as described in claim 1 wherein said circular profile of said generally cylindrical indention projecting onto said upper generally vertical surface extends along an arc that is less than 180°.

7. The method as described in claim 1 wherein said circular profile of said generally cylindrical indention projecting onto said upper generally vertical surface extends along an arc that is greater than 180°.

8. The method as described in claim 1 wherein said circular profile of said generally cylindrical indention projecting onto said upper generally vertical surface extends along an arc that is at least 80°.

9. The method as described in claim 1 wherein said circular profile of said generally cylindrical indention projecting onto said upper generally vertical surface extends along an arc that is 240° or less.

10. The method as described in claim 1 wherein said circular profile of said generally cylindrical indention projecting onto said upper generally vertical surface extends along an arc that is between 80° and 240°.

11. The method as described in claim 1 wherein said blind end comprises a closed end of said generally cylindrical indentation, and wherein said circular profile of said blind end extends 360°.

12. The method as described in claim 1 wherein each said outward side face of said posts defines a plurality of said generally cylindrical indentions.

13. A method of engaging a surgical tool having spaced apart jaws with inward facing tubular protrusions with a stabilization member connectable bone interfacing implant, said method comprising:

providing said implant with a body configured for interfacing with a bone structure and a head connected with said body, said head having spaced apart posts juxtaposed by a stabilization member receiving area, each said post having an outward side face, said outward side face having an upper generally vertical surface intersecting with a generally inward directed under surface intersecting with a lower generally vertical surface, said outward side face of each said post having at least one generally cylindrical indention intersecting said upper generally vertical surface and said inward directed under surface, said lower generally vertical surfaces of said posts being spaced apart a distance D1 and said upper generally vertical surfaces being spaced apart a distance D2 greater than said distance D1;

providing each said generally cylindrical indentions with a circular profile that projects onto and extends along said upper generally vertical surfaces over a 180° arc and defining an indentation window at said under surface having a window width D4, and providing said tubular protrusions with a radius closely approximating a radius of said generally cylindrical indentions, said tubular protrusions having a flattened region defining a protrusion width greater than said window width D4, said tubular protrusions defining a protrusion height perpendicular to said protrusion width that is less than said window width D4;

separating said tubular protrusions apart to define a separation distance therebetween closely approximating said distance D1;

positioning said tubular protrusions adjacent said generally lower vertical surfaces defined by said posts of said implant head;

displacing said tubular protrusions in an upward direction along said generally lower vertical surface toward said generally cylindrical indentions while maintaining said separation distance therebetween; and angling said surgical tool to generally align said protrusion height with said window width D4 and inserting said tubular protrusions through said indention windows to position said tubular protrusions within said generally cylindrical indentations, and straightening out said surgical tool to lock said tubular protrusions within said generally cylindrical indentions.

* * * * *